(12) United States Patent
McGovern

(10) Patent No.: US 6,535,823 B1
(45) Date of Patent: Mar. 18, 2003

(54) METHOD AND APPARATUS FOR DETERMINING LIPID RANCIDITY

(75) Inventor: Frank McGovern, Norwell, MA (US)

(73) Assignee: Omnion, Inc., Rockland, MA (US)

( * ) Notice: Subject to any disclaimer, the term of this patent is extended or adjusted under 35 U.S.C. 154(b) by 0 days.

(21) Appl. No.: 09/346,116

(22) Filed: Jul. 1, 1999

(51) Int. Cl.⁷ .................. G01N 31/00; G06F 19/00
(52) U.S. Cl. ...................... 702/22; 702/24; 702/25; 702/31; 73/863.01
(58) Field of Search ................. 702/19, 22–25, 702/30–31, 104; 422/69, 81, 98, 101; 436/60, 156; 324/438, 439; 73/61.41, 863.01

(56) References Cited

U.S. PATENT DOCUMENTS

| | | | | |
|---|---|---|---|---|
| 5,092,220 A | * | 3/1992 | Rounbehler | 436/156 |
| 5,172,332 A | * | 12/1992 | Hungerford et al. | 73/863.01 |
| 5,339,254 A | * | 8/1994 | Matlock et al. | 702/19 |
| 5,463,321 A | * | 10/1995 | Matlock et al. | 324/439 |
| 5,981,917 A | * | 11/1999 | Groth et al. | 219/497 |

OTHER PUBLICATIONS

The pH and conductivity handbook, vol. 29. OMEGA Engineering, Inc. 1995, Sections B–7 and D–30.*

* cited by examiner

Primary Examiner—Bryan Bui
(74) Attorney, Agent, or Firm—Nutter, McClennen & Fish LLP; William C. Geary, III; Jasbir Sagoo

(57) ABSTRACT

A method and apparatus is disclosed for determining the oxidative stability of pure lipids or lipids incorporated into complex matrices containing other, non-lipid ingredients. An exemplary test system includes a first container adapted to contain the sample and a heater for heating the sample to make it give off an effluent gas. A second container contains a collection fluid through which the effluent gas can be passed. A sensor within the second container measures pH, acetate, ammonia, and/or formate. An optional computation device in communication with the one or more sensors determines a point in time at which the level of one of pH, acetate, formate and/or ammonia changes suddenly. An exemplary method of predicting material stability includes the steps of: heating a sample of material including a lipid; passing a gas through the heated sample to provide effluent gas; passing the effluent gas through a collection fluid; and testing the collection fluid to determine the level of one of pH, acetate, formate and ammonia. In a subsequent step, a point in time at which the level of one of pH, acetate, formate and ammonia changes suddenly is identified.

7 Claims, 2 Drawing Sheets

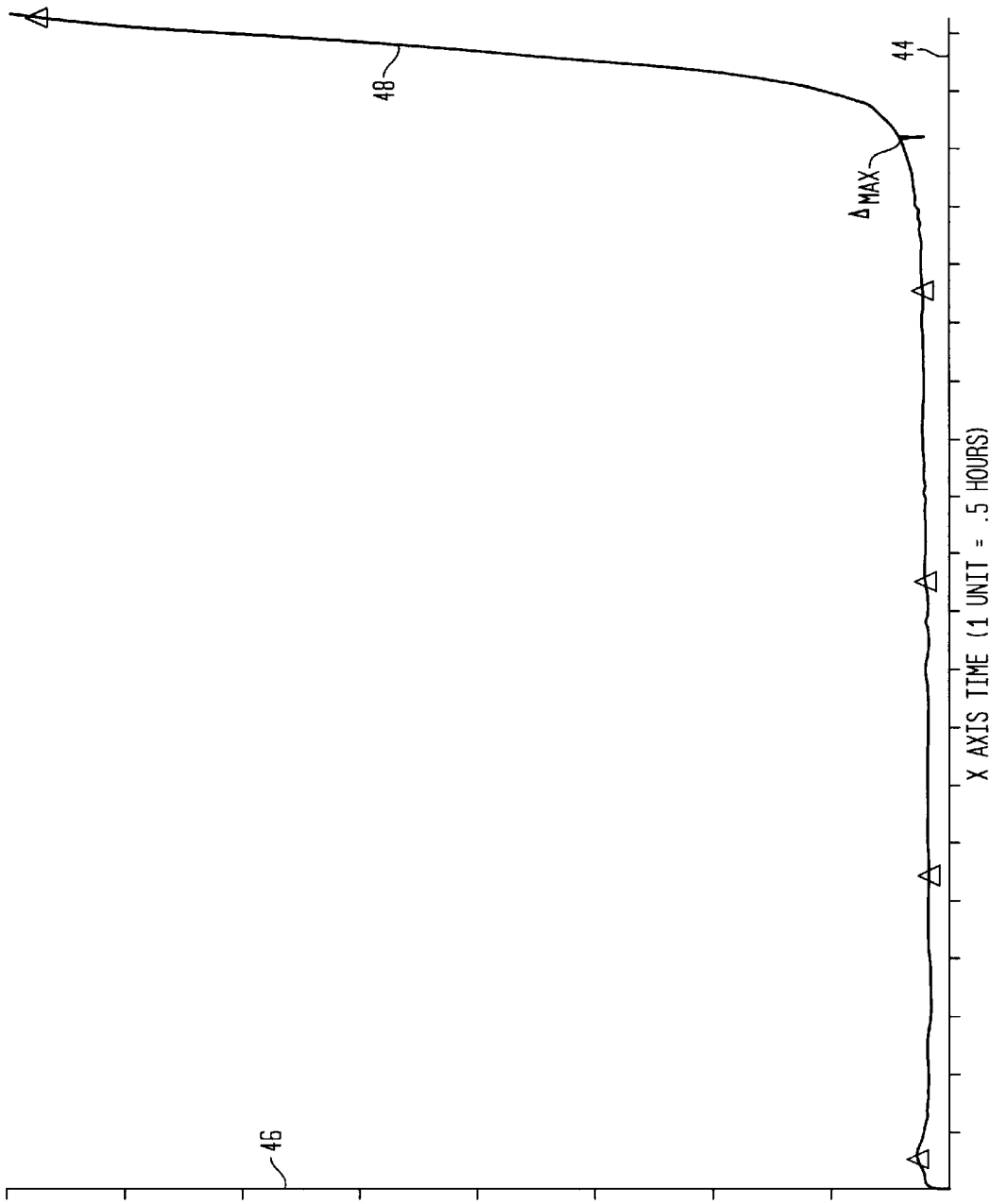

METHOD AND APPARATUS FOR DETERMINING LIPID RANCIDITY

CROSS-REFERENCE TO RELATED APPLICATIONS

Not Applicable.

STATEMENT REGARDING FEDERALLY SPONSORED RESEARCH

Not Applicable.

FIELD OF THE INVENTION

The present invention relates to an apparatus for determining the shelf-life of foods, and more particularly to a method and device for determining the stability of lipids.

BACKGROUND OF THE INVENTION

In the food industry, "shelf life" is a term used to describe the length of time a packaged food can be stored without deteriorating to a point that it is inedible due to taste or safety reasons. Many factors affect the shelf life of packaged food products. For example, processing techniques and chemical preservatives affect shelf life, as do moisture content and chemical composition of natural food ingredients. Additionally, almost all food products include one or more fats or lipids in liquid or solid form, the characteristics of which can greatly affect not only the nutritional quality and taste of the food, but also its shelf life.

Polyunsaturated fats, such as walnut oil, flaxseed oil, and fish oil oxidize readily and can become rancid in a few weeks or less, even if refrigerated. Therefore, these oils are almost universally shunned by food processors in favor of refined oils such as cottonseed oil, corn oil, and peanut oil that are hydrogenated or partially-hydrogenated to render them less readily oxidized, and therefore more stable. Although stability characteristics are of considerable importance with respect to edible lipids, they are also important with respect to inedible oils that have commercial applications, wherein the commercial value of the oil is affected by its stability.

All oils and fats have a resistance to oxidation which depends on their degree of saturation, natural or added antioxidants, pro-oxidants or prior abuse. Oxidation is slow until this resistance is overcome, at which point oxidation accelerates rapidly. The length of time before the onset of rapid acceleration is commonly referred to as the "induction period," or Oxidative Stability Index (OSI).

Instruments have been developed to help gauge or predict the stability of lipids by accelerating the development of oxidative rancidity so that the useful life of a lipid can be determined. Such an instrument for determining oxidative stability is disclosed in U.S. Pat. No. 5,339,254, wherein a lipid is forced to oxidize and the time for oxidation is measured. More specifically, the disclosed instrument works by heating a lipid sample and forcing air through it. Air exiting the oil is subsequently directed into water in which a conductivity sensor is immersed. The sensor measures a change in conductivity of the water caused by volatile, water-soluble materials emitted by the oxidizing oil. The measurement of the length of time that elapses from the start of the test, until the point of maximum change of rate of conductivity in the water, provides the OSI value at a selected temperature, for example: OSI=11.7 hours at 110° C.

Although the above-described apparatus and method may be suitable for determining the stability of pure lipids, it is not effective for measuring the stability of lipids which are components of more complex samples, because some of the other components also emit volatile, water-soluble materials that cause a change in conductivity. Thus, the instrument incorrectly identifies the onset of lipid oxidation and provides an unreliable OSI value. Notable among problematic sample types are protein-containing foods which emit volatile, alkaline materials, such as ammonia and a variety of amines, all of which increase water conductivity.

Another deficiency of the known apparatus is the great length of time required to perform a test. For example, typical OSI measurements on salad oils can take about sixteen hours, while hardened oils such as those contained in some margarine formulations can take several hundred hours.

Accordingly, there is a need for an improved method and apparatus capable of accurate measurement of the oxidative stability of lipids, either alone or in addition to other materials, as well as the ability to process and evaluate a sample much more quickly than known devices.

SUMMARY OF THE INVENTION

The present invention provides a method and apparatus for accurately predicting the oxidative stability of a pure lipid or a material including one or more lipids in addition to other ingredients. In an exemplary embodiment, a test system includes a first container adapted to contain the sample and a heater for heating the sample to make it give off an effluent gas. A second container contains a collection fluid through which the effluent gas can be passed and one or more sensors within the second container can measure pH, acetate, ammonia, and/or formate levels. An optional computation device in communication with the one or more sensors determines a point in time at which the level of pH, acetate, formate and/or ammonia changes suddenly.

Thus, an exemplary method of predicting material stability includes the steps of: heating a sample of material including a lipid; passing a gas through the heated sample to provide effluent gas; passing the effluent gas through a collection fluid; and testing the collection fluid to determine the level of pH, acetate, formate and/or ammonia. In a subsequent step, a point in time at which the level of one of pH, acetate, formate and/or ammonia changes suddenly is identified.

BRIEF DESCRIPTION OF THE DRAWINGS

The invention will be more fully understood from the following detailed description taken in conjunction with the accompanying drawings, in which:

FIG. 3 is a graphical representation of test data provided by the system of FIG. 1.

DETAILED DESCRIPTION OF THE INVENTION

Figure 1:
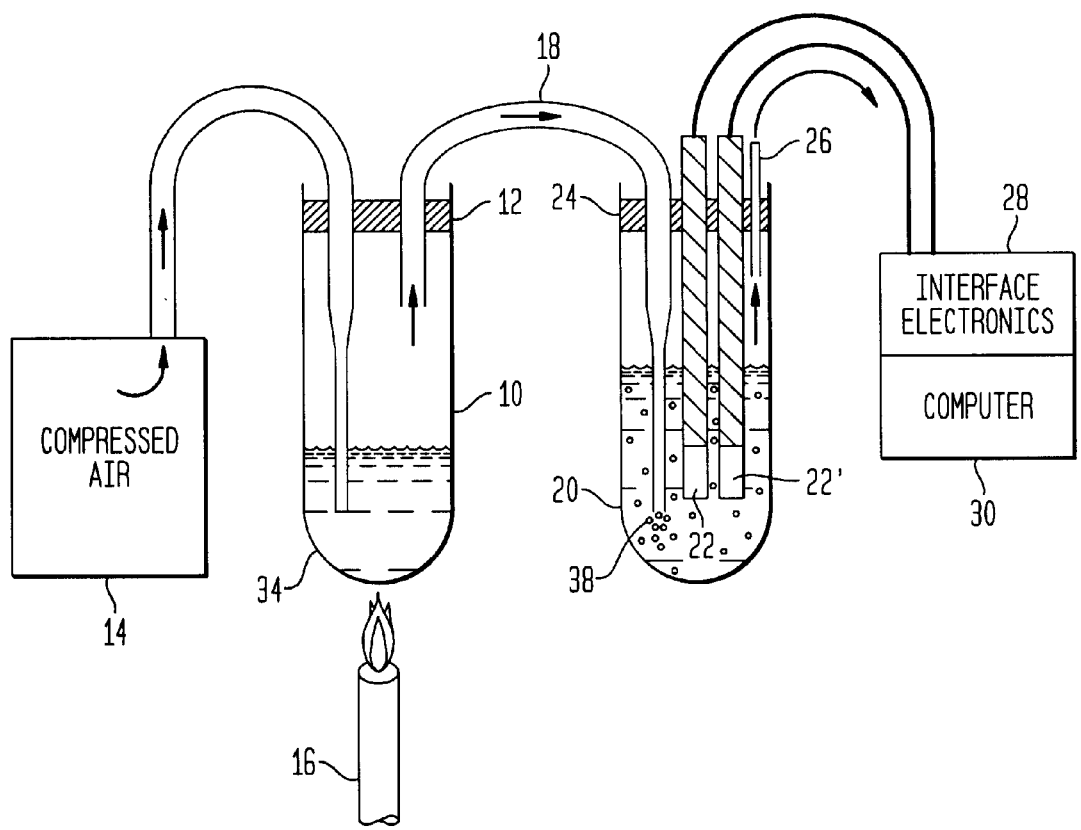
FIG. 1 is a schematic representation of a system in accordance with the present invention.

Referring to FIG. 1, a system in accordance with the present invention is illustrated. The system includes a first container 10, such as a glass test tube having a size and shape suitable for a sample to be tested. The first container 10 can be closed or sealed with an apertured stopper and provided one or more fluid flow paths (tube, channel, conduit, etc.) 12 for controlled passage of a gas into the first container.

Gas can be supplied to and enter the first container 10 directly from the atmosphere, from an air compressor, or from a gas supply line or bottle. The gas includes oxygen and it is passed into the first container at a rate sufficient to ensure that any oxidation reaction that may occur during a test is not limited by an inadequate supply of oxygen. In an exemplary system, a compressor 14 forces atmospheric air into the first container 10 having a volume of 75 ml at about 140 ml of air per minute. Depending upon the oxygen content of the gas, the flow rate can be modified.

A heat source 16, integral to the first container 10 or separate therefrom, is provided to heat the first container and/or the contents of the container. Although the illustration depicts a flame, the heat source 16 can be an electric element or any other heat source known in the art. In the exemplary system, the heat source 16 is capable of maintaining a sample temperature within 0.1° C. at temperatures ranging from 40° C. to 220° C. for hundreds of hours. However, most tests are conducted at 110° C. or 130° C.

A tube 18 provides a gas flow path to exhaust or remove gas from the first container 10 and transfer it into a second container 20.

The second container 20 can be a glass test tube having a volume of about 100 ml for containing a collection fluid, receiving gas from the first container 10, and receiving a sensor 22. The second container 20 can be closed or sealed with an apertured stopper 24 and provided one or more fluid flow paths 26 (tube, channel, conduit, etc.) for controlled venting of gas from the second container into the atmosphere as shown, or into an exhaust gas collection system or tank as is known in the art.

The sensor 22 disposed within the second container can be placed in communication with support or interface electronics 28 for processing the output of the sensor (as is known in the art) to display sensor readings, provide output signals for further processing, or both. A computer 30, capable of processing signals output from the support electronics 28 and one or more sensors 22, can be provided to store and process data, as well as to provide a user readable output in the form of charts, tables, calculated values, and the like. Although a computer or other device capable of monitoring sensor output over time can be quite valuable, a computer is not needed to perform an analysis; it can be done with pencil and paper.

The sensor 22 is selected depending upon the type of analysis desired. A second sensor 22' (as well as third, or fourth sensor) is provided as required if different properties or materials are to be detected. Exemplary sensors 22, 22' include pH, formate, acetate, and ammonia sensors that are deployed individually or in combination.

Figure 2:
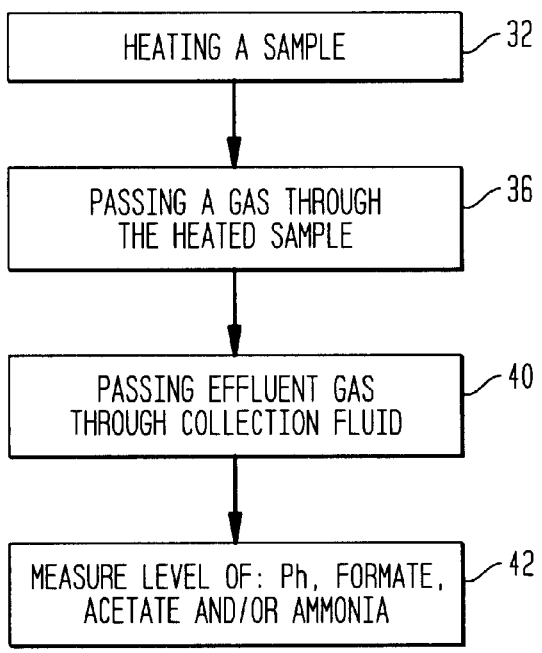
FIG. 2 is a flowchart of method steps in accordance with the invention.

An exemplary method of performing an analysis using the system described above with respect to FIG. 1 includes the following steps as illustrated in FIG. 2. In a first step 32, a sample of material 34 (hereinafter "sample") that is to be evaluated is placed in the first container 10. The sample 34 can be in liquid form as shown, or in ground-up, solid form. The sample can also be mixed with a carrier material.

In a second step 36, the first container 10 is closed and heated causing the sample 34 to give off a gaseous effluent that includes volatile organic acids and other compounds such as ammonia, acetate, and formate that are detectable by one or more of the selected sensors 22, 22'. Generally concurrent with the second step 36, or as a part thereof, oxygen containing gas is caused to flow into the first container 10 and to bubble through the sample 34. The effluent gas entrained by the air passes through the tube 18 and into the second container 20 that is at least partially filled with a collection fluid 38 such as water, glycerine and water, or a buffered solution. The gaseous effluent from the sample then goes into solution in the collection fluid 38.

In a third step 40, one or more sensors 22, 22' are activated to detect materials in, or measure properties of, the collection fluid 38 to provide sensed values or levels.

In a fourth step 42, the sensed values or levels are monitored over time until a sudden change in the sensed value or level is detected; and the time at which the sudden change occurs is noted (i.e., the OSI time). This step can be performed by hand with pencil and paper, or with a computer. As used herein "sudden" is defined as the point of maximum rate of change in the sensed value.

Thus, in an exemplary test, a 25 gram sample of AAFCO 9728 HORSE SUPL 11 is placed into the first container and is heated to 130° C., while a gas mixture including about 20.9% oxygen by volume (ordinary air) is directed through the sample at or greater than 135 ml per minute. Air containing volatile material (effluent gas) from the sample passes into the second container filled with 50 ml of deionized water, so as to bubble through the water. A pH sensor is disposed within the second container and is at least partially immersed in the water to measure the acidity of the water. Over time, lipid oxidation causes the pH of the water to decrease and measurements are taken until a sudden change occurs in the pH value.

FIG. 3 illustrates the change in pH over time for the preceding example, wherein the x-axis indicates time and the y-axis 46 indicates pH level. The plotted curve 48 illustrates the pH values over time and the point $\Delta_{max}$ indicates the time of sudden change in pH that is indicative of rapid oxidation of the lipid in the sample. In this test, the OSI value is 9.1 at 130° C.

A system that measures and evaluates pH is a significant improvement over a system that analyses conductivity with respect to complex samples and pure lipids because the measurement of pH can be performed in about half the time as a conductivity measurement. Therefore, by analyzing pH instead of conductivity, weeks of analysis time can be saved and system throughput can be doubled. Additionally, pH is an improvement over conductivity because changes in pH are directional, thereby providing a way to distinguish the formation of volatile acid species indicative of lipid oxidation from the formation of alkaline species indicative of protein reactions. By contrast conductivity always changes in the same direction (i.e., it increases for both of the above described reactions). Furthermore, pH detection is inherently several order of magnitude more sensitive than conductivity allowing changes in the collection fluid to be detected much more quickly than with conductivity measurement.

However, a limitation of pH detection is that a net change is measured which may reflect the interaction of the products of lipid oxidation with the products of protein decomposition or oxidation. For some samples, both processes occur simultaneously, and with more alkali being formed, it is not possible to determine the onset of the formation of acids. Therefore, a second sensor 22' can be provide to detect ammonia. If the rate of increase of pH diminishes while the concentration of ammoniacal species increases, then the OSI time is the time corresponding to the time of the pH rate change.

Additionally, third and fourth sensors may be provided to measure, acetate and formate concentrations or the first and second sensors can measure acetate and formate without monitoring ammonia or pH. The concentration of acetate and formate increase rapidly as lipids begin to oxidize and the measurement thereof is not adversely affected by the formation of alkaline materials. Collecting the effluent air in collection fluid that is mildly alkaline with respect to formic and acetic acids insures that these weak acids yield all of their formate and acetate amines and maximizes instrument sensitivity.

Thus, it is seen that measuring and evaluating the change of different properties can provide the capability of accurately determining lipid oxidation. However, as oxidative stability is of widespread interest in the areas of medicine and nutrition, of fuels and lubricants, and in the cosmetic, pharmaceutical and general chemical industries, the testing of oils is not restricted to edible fats and oils.

Although the invention has been shown and described with respect to exemplary embodiments, various other changes, omissions and additions in form and detail may be made without departing from the spirit and scope of the invention. All publications and references cited herein are expressly incorporated herein by reference in their entirety.

What is claimed is:

1. A method for evaluating a sample of material that includes a lipid, comprising the steps of:
    heating the sample;
    passing a gas through the heated sample to provide effluent gas;
    passing the effluent gas through a collection fluid; and
    testing the collection fluid to determine the level of ammonia and the level of at least one of pH, acetate, and formate.

2. The method of claim 1, further comprising the step of plotting the level of ammonia and the level of at least one of pH, acetate, and formate over time.

3. The method of claim 1, further comprising the step of determining a point in time at which the level of ammonia and the level of at least one of pH, acetate, and formate changes suddenly.

4. The method of claim 1, further comprising the step of determining points in time at which the level of ammonia and the levels of at least two of pH, acetate, and formate change suddenly.

5. The method of claim 1, further comprising the step of determining points in time at which the level of ammonia and the levels of pH, acetate, and formate change suddenly.

6. A system for evaluating a sample of material that includes a lipid, the system comprising:
    a sensor for determining one of a level of ammonia and the level of at least one of pH, acetate, and formate; and
    a computation device in communication for determining a point in time at which the level of ammonia and the level of at least one of pH, acetate, and formate changes suddenly.

7. A system for evaluating a sample of material that includes at least one lipid, the system comprising:
    a first container adapted to contain the sample;
    a heater for heating the first container to cause the sample to give off an effluent gas;
    a second container for containing a collection fluid;
    a conduit for transferring the effluent gas from the first container to the second container and into the collection fluid;
    a sensor selected from the group of sensors consisting of a pH sensor, an acetate sensor, an ammonia sensor, and a formate sensor, wherein the sensor is within the second container and at least partially submersible in the collection fluid; and
    a computation device in communication with the sensor for determining a point in time at which the level of ammonia and the level of at least one of pH, acetate, and formate changes suddenly.

* * * * *